US012678491B2

(12) United States Patent
Lagresle-Peyrou et al.

(10) Patent No.: US 12,678,491 B2
(45) Date of Patent: Jul. 14, 2026

(54) METHODS FOR INDUCING FULL ABLATION OF HEMATOPOIESIS

(71) Applicants: INSERM (INSTITUT NATIONAL DE LA SANTÉ ET DE LA RECHERCHE MÉDICALE), Paris (FR); FOUNDATION IMAGINE, Paris (FR); ASSISTANCE PUBLIQUE-HÔPITAUX DE PARIS (APHP), Paris (FR); UNIVERSITÉ DE PARIS, Paris (FR); UNIVERSITÉ TOULOUSE III—PAUL SABATIER, Paris (FR)

(72) Inventors: Chantal Lagresle-Peyrou, Paris (FR); Aurélien Olichon, Toulouse (FR); Hanem Sadek-Rock, Paris (FR); Isabelle Andre, Paris (FR); Marina Cavazzana, Paris (FR)

(73) Assignees: INSERM (INSTITUT NATIONAL DE LA SANTÉ ET DE LA RECHERCHE MÉDICALE), Paris (FR); FONDATION IMAGINE, Paris (FR); ASSISTANCE PUBLIQUE—HÔPITAUX DE PARIS (APHP), Paris (FR); UNIVERSITÉ DE PARIS, Paris (FR); UNIVERSITÉ TOULOUSE III—PAUL SABATIER, Toulouse (FR)

( * ) Notice: Subject to any disclaimer, the term of this patent is extended or adjusted under 35 U.S.C. 154(b) by 1028 days.

(21) Appl. No.: 17/627,771

(22) PCT Filed: Jul. 17, 2020

(86) PCT No.: PCT/EP2020/070244
§ 371 (c)(1),
(2) Date: Jan. 17, 2022

(87) PCT Pub. No.: WO2021/009336
PCT Pub. Date: Jan. 21, 2021

(65) Prior Publication Data
US 2022/0265781 A1 Aug. 25, 2022

(30) Foreign Application Priority Data

Jul. 18, 2019 (EP) .................................... 19305948

(51) Int. Cl.
*A61K 38/46* (2006.01)
*A61P 35/00* (2006.01)
*C12N 9/14* (2006.01)

(52) U.S. Cl.
CPC .............. *A61K 38/46* (2013.01); *A61P 35/00* (2018.01); *C12N 9/14* (2013.01); *C12Y 306/05002* (2013.01)

(58) Field of Classification Search
None
See application file for complete search history.

(56) References Cited

FOREIGN PATENT DOCUMENTS

WO 2014017106 A1 1/2014
WO 2016164502 A1 10/2016

OTHER PUBLICATIONS

Bacigalupo et al. (Blood and Marrow transplant 15; 1628-1633 (2009) teach myeloblative conditioning (which is another name for fully ablative hematopoiesis in the context of bone marrow and transplantation).*
The Merck Manual (https://www.merckmanuals.com/professional/hematology-and-oncology/leukemias/acute-myeloid-leukemia-aml?query=AML accessed Apr. 4, 2025).*
Gu Y et al, "Biochemical and biological characterization of a human Rac2 GTPase mutant associated with phagocytic immunodeficiency", Journal of Biological Chemistry, American Society for Biochemistry and Molecular Biology, US, vol. 276, No. 19, Feb. 22, 2001 (Feb. 22, 2001), p. 15929-15938,.
Daria Illenberger et al, "Rac2 Regulation of Phospholipase C-[beta] 2 Activity and Mode of Membrane Interactions in Intact Cells", Journal of Biological Chemistry, vol. 278, No. 10, Mar. 7, 2003 (Mar. 7, 2003), p. 8645-8652.

* cited by examiner

*Primary Examiner* — Tara L Martinez
(74) *Attorney, Agent, or Firm* — WCF IP

(57) ABSTRACT

The inventors have identified an autosomal dominant (AD) missense mutation in the RAC2 gene (coding for Ras-related botulinum toxin substrate 2 (RAC2)) in three Severe combined immunodeficiencies (SCID) patients whose clinical presentation overlaps with the RD SCID form but who lack AK2 mutations and deafness. Using biochemical and in vitro differentiation assays, the inventors demonstrated that the RAC2 mutation was closely related to an impairment in cell differentiation capacity and defects in cellular and mitochondrial networks. Taken as a whole, the data demonstrate that a dominant gain-of-function (GOF) mutation in the RAC2 protein's GDP/GTP binding site inhibits HSPC differentiation and leads to a severe AD form of SCID with a clinical presentation of RD. Accordingly, the results prompt to consider that introduction of the identified RAC2 mutein in the hematopoietic lineage would be suitable for inducing full ablation of hematopoiesis.

Figures 1A, 1B:
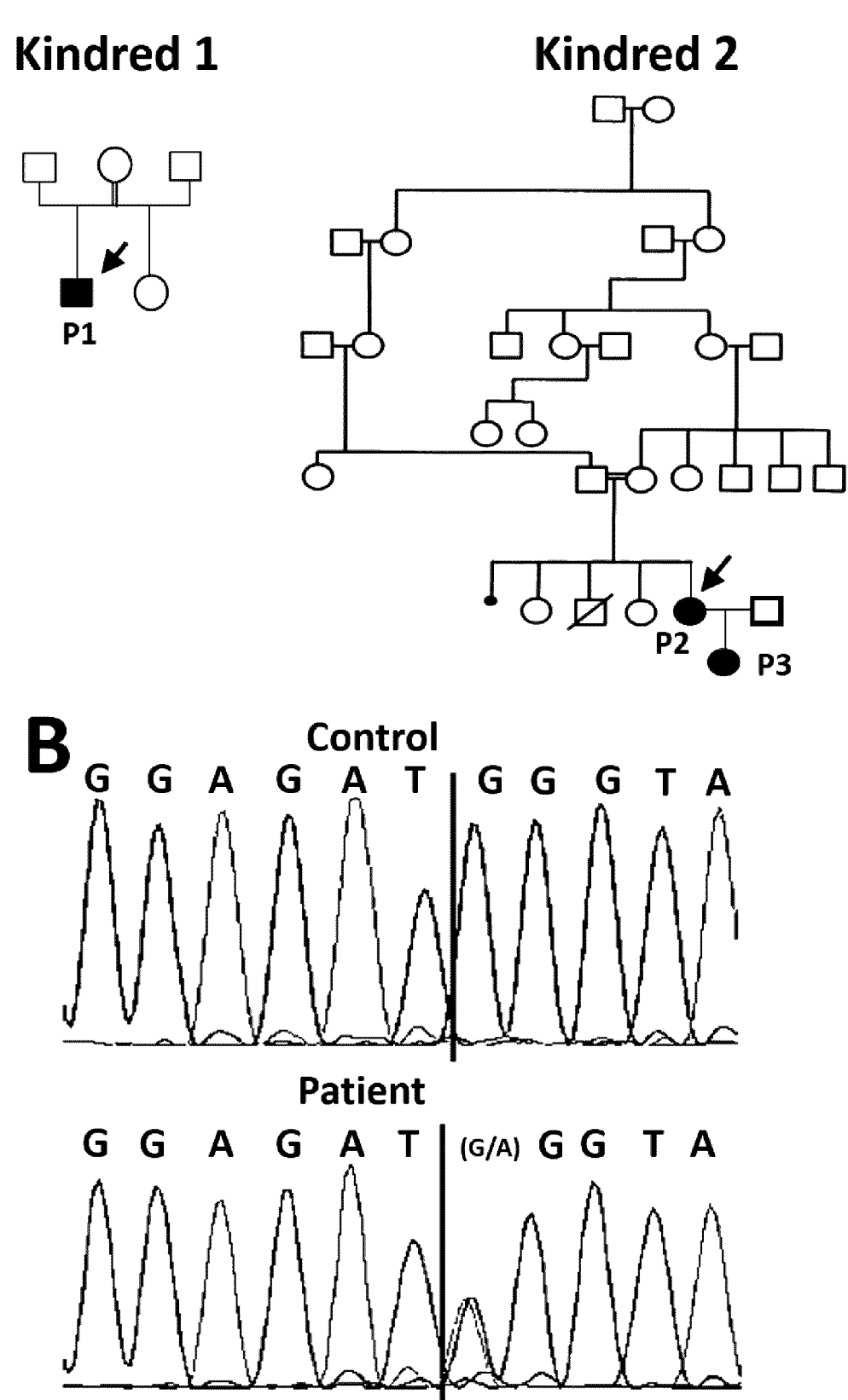

6 Claims, 9 Drawing Sheets
Specification includes a Sequence Listing.

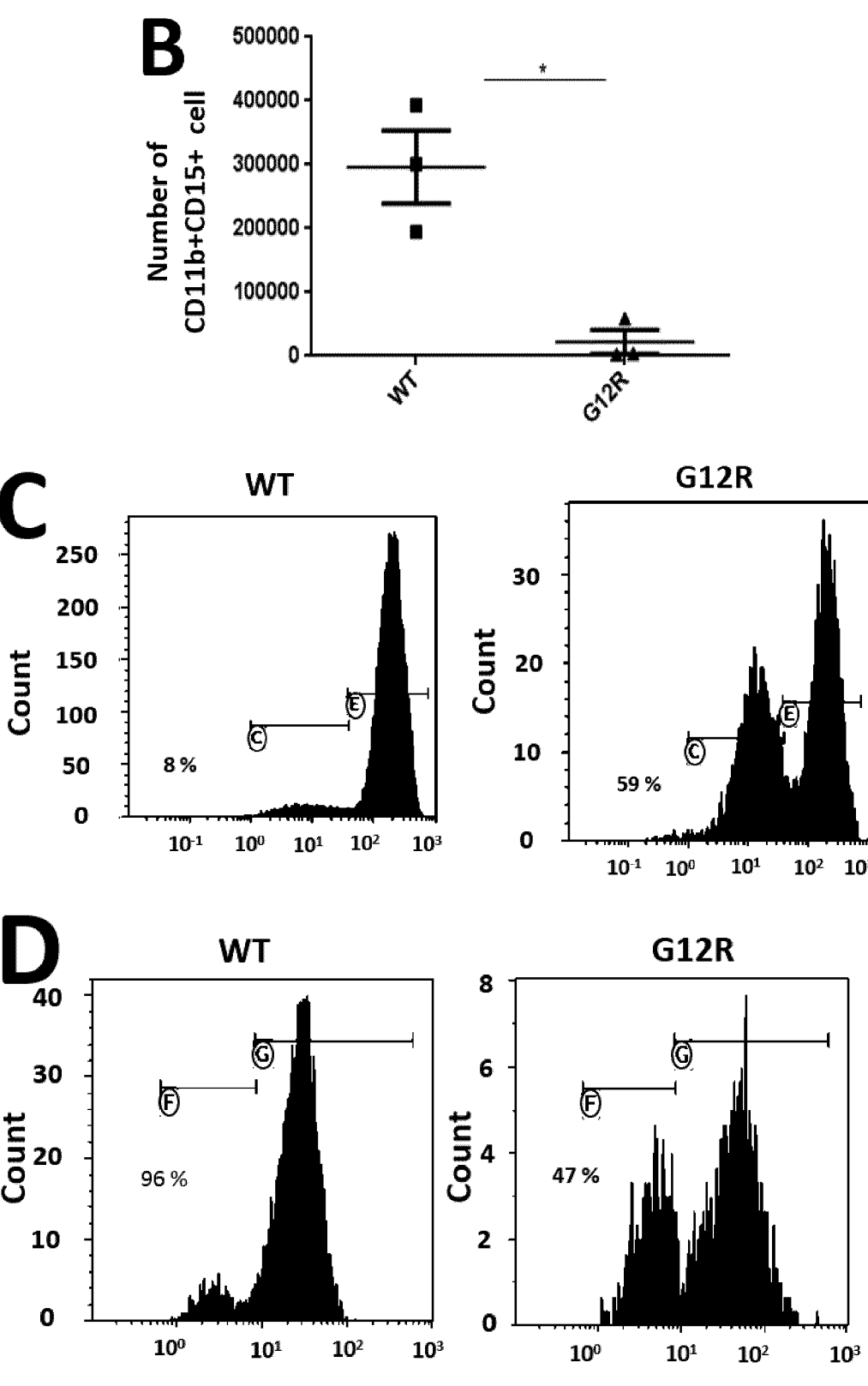
Figures 5B-D

SEQUENCE LISTING

<160> NUMBER OF SEQ ID NOS: 3

<210> SEQ ID NO 1
<211> LENGTH: 192
<212> TYPE: PRT
<213> ORGANISM: Homo sapiens

<400> SEQUENCE: 1

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80
```

```
Cys Phe Ser Leu Val Ser Pro Ala Ser Tyr Glu Asn Val Arg Ala Lys
                85              90              95

Trp Phe Pro Glu Val Arg His His Cys Pro Ser Thr Pro Ile Ile Leu
            100             105             110

Val Gly Thr Lys Leu Asp Leu Arg Asp Asp Lys Asp Thr Ile Glu Lys
            115             120             125

Leu Lys Glu Lys Lys Leu Ala Pro Ile Thr Tyr Pro Gln Gly Leu Ala
        130             135             140

Leu Ala Lys Glu Ile Asp Ser Val Lys Tyr Leu Glu Cys Ser Ala Leu
145             150             155             160

Thr Gln Arg Gly Leu Lys Thr Val Phe Asp Glu Ala Ile Arg Ala Val
            165             170             175

Leu Cys Pro Gln Pro Thr Arg Gln Gln Lys Arg Ala Cys Ser Leu Leu
            180             185             190

<210> SEQ ID NO 2
<211> LENGTH: 11
<212> TYPE: DNA
<213> ORGANISM: Homo sapiens

<400> SEQUENCE: 2
ggagatgggt a                                                          11

<210> SEQ ID NO 3
<211> LENGTH: 11
<212> TYPE: DNA
<213> ORGANISM: Homo sapiens
<220> FEATURE:
<221> NAME/KEY: misc_feature
<222> LOCATION: (7)..(7)
<223> OTHER INFORMATION: N is G or A

<400> SEQUENCE: 3
ggagatnggt a                                                          11
```

METHODS FOR INDUCING FULL ABLATION OF HEMATOPOIESIS

FIELD OF THE INVENTION

The present invention is in the field of haematology.

BACKGROUND OF THE INVENTION

Hematopoietic stem cell transplantation (HSCT) is a potentially curative therapeutic approach for a variety of malignant and non-malignant hematopoietic diseases. When HSCT is performed in patients with malignant disorders, preparative or conditioning regimens are administered as part of the procedure to achieve 3 goals: make space in the bone-marrow (myeloablation), provide sufficient immunoablation to prevent graft rejection and reduce the tumor burden. The intensity of conditioning regimens can vary substantially, and when selecting the optimal conditioning regimen for any given patient, disease-related factors such as diagnosis and remission status, as well as patient-related factors including age, donor availability, and presence of comorbid conditions, need to be considered. Although full consensus has not been reached within the HCT community, conditioning regimens have been classified as high-dose (myeloablative), reduced-intensity, and non-myeloablative. For instance myeloablative, or "high-dose" regimens, consisting of alkylating agents (single or multiple) with or without total body irradiation, are expected to ablate hematopoiesis, not allowing autologous hematologic recovery. The administration of conditioning regimens is associated with immediate and delayed toxicities. For instance, nausea, vomiting, transient acute parotiditis, xerostomia, mucositis, and diarrhea are commonly observed acute complications. Interstitial pneumonitis, idiopathic pulmonary fibrosis, and reduced lung pulmonary function can also be observed. The occurrence of sinusoidal obstruction syndrome (also known as veno-occlusive disease of the liver) is more common in chemotherapy-based regimens. Long-term side effects include infertility, cataract formation, hypothyroidism and thyroiditis, and secondary malignancies. Accordingly, there is a need for new method that will allow full ablation of hematopoiesis with a minimal occurrence of short and long term severe adverse side effects.

RAC2 belongs to the Rac subfamily of the Rho family of small GTPases. In the inactive GDP-bound state, RAC2 is located in the cytosol. Upon stimulation and activation by guanine nucleotide exchange factors, the active RAC2-GTP-bound form is translocated to the plasma membrane. There, RAC2 triggers various signalling pathways until the GTP is hydrolysed or the GTPase is degraded by the cell[7-9]. Unlike the other members of the Rac subfamily (RAC1 and RAC3), expression of RAC2 is restricted to the hematopoietic lineage[10,11].

SUMMARY OF THE INVENTION

As defined by the claims, the present invention relates to methods for inducting full ablation of hematopoiesis and uses thereof in the conditioning for bone marrow transplantation and the treatment of hematopoietic cell malignancies.

DETAILED DESCRIPTION OF THE INVENTION

The inventors have identified an autosomal dominant (AD) missense mutation in the RAC2 gene (coding for Ras-related C3 botulinum toxin substrate 2 (RAC2)) in three Severe combined immunodeficiencies (SCID) patients whose clinical presentation overlaps with the RD SCID form but who lack AK2 mutations and deafness. Using biochemical and in vitro differentiation assays, the inventors demonstrated that the RAC2 mutation was closely related to an impairment in cell differentiation capacity and defects in cellular and mitochondrial networks. Taken as a whole, the data demonstrate that a dominant gain-of-function (GOF) mutation in the RAC2 protein's GDP/GTP binding site inhibits HSPC differentiation and leads to a severe AD form of SCID with a clinical presentation of RD. Accordingly, the results prompt to consider that introduction of the identified RAC2 mutein in the hematopoietic lineage would be suitable for inducing full ablation of hematopoiesis.

The first object of the present invention relates to a method of full ablating hematopoiesis in a patient in need thereof comprising administering to the patient a therapeutically effective amount of i) a polypeptide comprising the amino acid sequence as set forth in SEQ ID NO:1 wherein the amino residue (G) at position 12 is mutated, or ii) a polynucleotide encoding for a polypeptide comprising the amino acid sequence as set forth in SEQ ID NO:1 wherein the amino residue (G) at position 12 is mutated.

A further object of the present invention relates to a method for inhibiting proliferation and differentiation of a population of hematopoietic stem cells comprising contacting said population with an effective amount of i) a polypeptide comprising the amino acid sequence as set forth in SEQ ID NO:1 wherein the amino residue (G) at position 12 is mutated, or ii) a polynucleotide encoding for a polypeptide comprising the amino acid sequence as set forth in SEQ ID NO:1 wherein the amino residue (G) at position 12 is mutated.

A further object of the present invention relates to a method of inducing cell death of a population of hematopoietic cells comprising contacting said population with an effective amount of i) a polypeptide comprising the amino acid sequence as set forth in SEQ ID NO:1 wherein the amino residue (G) at position 12 is mutated, or ii) a polynucleotide encoding for a polypeptide comprising the amino acid sequence as set forth in SEQ ID NO:1 wherein the amino residue (G) at position 12 is mutated.

A further object of the present invention relates to a method of inducing cell death of a population of malignant hematopoietic cells comprising contacting said population with an effective amount of i) a polypeptide comprising the amino acid sequence as set forth in SEQ ID NO:1 wherein the amino residue (G) at position 12 is mutated, or ii) a polynucleotide encoding for a polypeptide comprising the amino acid sequence as set forth in SEQ ID NO:1 wherein the amino residue (G) at position 12 is mutated.

A further object of the present invention relates to a method of treating a hematopoietic cell malignancy in a patient in need thereof comprising administering to the patient a therapeutically effective amount of i) a polypeptide comprising the amino acid sequence as set forth in SEQ ID NO:1 wherein the amino residue (G) at position 12 is mutated, or ii) a polynucleotide encoding for a polypeptide comprising the amino acid sequence as set forth in SEQ ID NO:1 wherein the amino residue (G) at position 12 is mutated.

As used herein, the term "hematopoietic cell" has its general meaning in the art and refers to any type of cell of the hematopoietic system, including, but not limited to, undifferentiated cells such as hematopoietic stem cells and progenitor cells, and differentiated cells e.g. leukocytes (for example granulocytes, monocytes and lymphocytes) platelets and red blood cells.

As used herein, the term "hematopoietic stem cell" or "HSC" refers to blood cells that have the capacity to self-renew and to differentiate into precursors of circulating mature blood cells. These precursor cells are immature blood cells that cannot self-renew and differentiate into circulating mature blood cells. Within the bone marrow microenvironment, the stem cells self-renew and maintain continuous production of hematopoietic cells that give rise to all mature blood cells throughout life. In some embodiments, the hematopoietic progenitor cells or hematopoietic stem cells are isolated form peripheral blood cells.

As used herein, the term "hematopoiesis" refers to the formation and development of hematopoietic cells involving proliferation and/or differentiation from stem cells.

Typically, the patient is selected from the group consisting of children, young adults, middle aged adults, and the elderly adults.

In some embodiments, the method of the present invention is particularly suitable for preparing the patient to bone marrow transplantation (i.e. conditioning treatment). The method of the present invention is thus particularly suitable for avoiding use of chemotherapy and radiotherapy. The method of the present invention will help bone marrow for new blood stem cells to grow, helps prevent the patient's body from rejecting the transplanted cells, and helps kill any cancer cells that could be present in the body. Typically, the administration of the Polypeptide or polynucleotide is performed before bone marrow transplantation.

As used herein, the term "bone marrow transplantation" or "hematopoietic stem cell transplantation" used herein should be considered as interchangeable, referring to the transplantation of hematopoietic stem cells in some form to a recipient. The hematopoietic stem cells do not necessarily have to be derived from bone marrow, but could also be derived from other sources such as umbilical cord blood or mobilized PBMC. As used herein, the terms "hematopoietic stem cell transplantation" or "HSCT" refer to a component of the treatment of a wide array of hematologic disorders. Generally, there are two types of HSCTs: autologous and allogeneic transplantation. As used herein, the term "allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor. Allogeneic transplantation involves infusion of donor stem cells, typically using a donor that matches the recipient's MHC. As used herein, the term "autologous" refers to deriving from or originating in the same patient. An "autologous transplant" refers to collection and retransplant of a patient's own cells or organs.

Examples of hematopoietic cell malignancies that are cancers include leukemias, lymphomas and multiple myelomas. Examples of leukemias include acute lymphoblastic leukemia (ALL), acute myelogenous leukemia (AML) and chronic myelogenous leukemia (CIVIL). Examples of lymphomas include Hodgkin's disease and its subtypes; non-Hodgkin lymphomas and its subtypes including chronic lymphocytic leukemia (CLL), small lymphocytic lymphoma (SLL), diffuse large B-cell lymphoma (DLBCL), follicular lymphoma (FL), mantle cell lymphoma (MCL), hairy cell leukemia (HCL), marginal zone lymphoma (MZL), Burkitt's lymphoma (BL), Post-transplant lymphoproliferative disorder (PTLD), T-cell prolymphocytic leukemia (T-PLL), B-cell prolymphocytic leukemia (B-PLL), Waldenstrom's macroglobulinemia/Lymphoplasmacytic lymphoma and other natural killer cell (NK-cell) or T-cell lymphomas. Examples of other malignant conditions which are hematopoietic cell malignancies include myelodysplastic syndrome (MDS); myeloproliferative diseases such as polycythemia vera (i.e., PV, PCV or polycythemia rubra vera (PRV)), essential thrombocytosis (ET), myelofibrosis; and diseases with features of both myelodysplastic syndromes and myeloproliferative diseases such as chronic myelomonocytic leukemia (CMML), juvenile myelomonocytic leukemia (JMML), atypical chronic myeloid leukemia (aCML) and myelodysplastic/myeloproliferative disease.

In particular the acute myelogenous leukemia (AML) hematopoietic cell malignancy is impacted by the mutation herein described.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "Rac2" has its general meaning in the art and refers to Ras-related C3 botulinum toxin substrate 2. An exemplary amino acid sequence for the human Rac2 is represented by SEQ ID NO:1.

```
>sp|P15153|Rac2_HUMAN Ras-related C3 botulinum
toxin
substrate 2 OS = Homo sapiens OX = 9606 GN = Rac2
PE = 21 SV = 1
                                    SEQ ID NO: 1
MQAIKCVVVGDGAVGKTCLLISYTTNAFPGEYIPTVFDNYSANVMVDSK

PVNLGLWDTAGQEDYDRLRPLSYPQTDVFLICFSLVSPASYENVRAKWF
```

5

-continued

```
PEVRHHCPSTPIILVGTKLDLRDDKDTIEKLKEKKLAPITYPQGLALAK

EIDSVKYLECSALTQRGLKTVFDEAIRAVLCPQPTRQQKRACSLL
```

As used herein, the term "mutation" has its general meaning in the art and refers to a substitution, deletion or insertion. The term "substitution" means that a specific amino acid residue at a specific position is removed and another amino acid residue is inserted into the same position. The term "deletion" means that a specific amino acid residue is removed. The term "insertion" means that one or more amino acid residues are inserted before or after a specific amino acid residue, more specifically, that one or more, preferably one or several, amino acid residues are bound to an a.-carboxyl group or an a,-amino group of the specific amino acid residue.

In some embodiments, the amino residue (G) at position 12 is substituted. In some embodiments, the amino residue (G) at position 12 is substituted by an amino acid residue (R).

As used herein, the term "polypeptide" has its general meaning in the art and refers to a polymer of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

As used herein, the term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In some embodiments, the polynucleotide comprises an mRNA. In other aspect, the mRNA is a synthetic mRNA. In some embodiments, the synthetic mRNA comprises at least one unnatural nucleobase. In some embodiments, all nucleobases of a certain class have been replaced with unnatural nucleobases (e.g., all uridines in a polynucleotide disclosed herein can be replaced with an unnatural nucleobase, e.g., 5-methoxyuridine). In some embodiments, the polynucleotide (e.g., a synthetic RNA or a synthetic DNA) comprises only natural nucleobases, i.e., A, C, T and G in the case of a synthetic DNA, or A, C, T, and U in the case of a synthetic RNA.

In some embodiments, the polynucleotide of the present invention is a messenger RNA (mRNA).

In some embodiments, the polynucleotide is inserted in a vector, such as a plasmid, cosmid, episome, artificial chromosome, phage or a viral vector. Typically, the vector is a viral vector which is an adeno-associated virus (AAV), a retrovirus, bovine papilloma virus, an adenovirus vector, a lentiviral vector, a vaccinia virus, a polyoma virus, or an infective virus. Typically, the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

In some embodiments, the polypeptide or polynucleotide of the present invention can be conjugated to at least one other molecule. Typically, said molecule is selected from the group consisting of polynucleotides, polypeptides, lipids, lectins, carbohydrates, vitamins, cofactors, and drugs. In some embodiments, the polypeptide or the polynucleotide of the present invention is conjugated to a molecule having a specific affinity for hematopoietic cells, such as antibodies or peptides having a binding affinity for a protein expressed at the surface of a hematopoietic stem cell. Conjugation can result in increased stability and/or half-life and can be particularly useful in targeting the polypeptide or the polynucleotides to hematopoietic cells.

By a "therapeutically effective amount" is meant a sufficient amount of the active ingredient for treating or reducing the symptoms at reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the active ingredient of the present invention (i.e. the polypeptide or polynucleotide) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In some embodiments, the polypeptide or polynucleotide of the present invention is formulated with lipidoids. The synthesis of lipidoids has been extensively described (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci US A. 2011 108:12996-3001). While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010), the present disclosure describes their formulation and use in delivering polynucleotides.

In some embodiments, the polypeptide or polynucleotide of the present invention is formulated using one or more liposomes, lipoplexes, or lipid nanoparticles.

Liposomes are artificially-prepared vesicles which can primarily be composed of a lipid bilayer and can be used as a delivery vehicle for the administration of pharmaceutical formulations. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the pharmaceutical formulations. As a non-limiting example, liposomes such as synthetic membrane vesicles are prepared by the methods, apparatus and devices described in US Patent Publication No. US20130177638, US20130177637, US20130177636, US20130177635, US20130177634, US20130177633, US20130183375, US20130183373 and US20130183372. In some embodiments, the liposomes are formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylamino-ethyl)-[1,3]-dioxolane (DLin-KC2-DMA), and MC3 (as described in US20100324120) and liposomes which can deliver small molecule drugs such as, but not limited to, DOXIL® from Janssen Biotech, Inc. (Horsham, Pa.). The polypeptide of polynucleotide of the present invention can be encapsulated by the liposome and/or it can be contained in an aqueous core which can then be encapsulated by the liposome (see International Pub. Nos. WO2012031046, WO2012031043, WO2012030901 and WO2012006378 and US Patent Publication No. US20130189351, US20130195969 and US20130202684).

In some embodiments, the polynucleotide of the present invention is formulated with stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, the polynucleotide of the present invention is formulated in a lipid nanoparticle such as those described in International Publication No. WO2012170930. Lipid nanoparticle formulations typically comprise a lipid, in particular, an ionizable cationic lipid, and further comprise a neutral lipid, a sterol and a molecule capable of reducing particle aggregation, for example a PEG or PEG-modified lipid. The lipid can be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid is a cationic lipid such as, but not limited to, DLin-DMA, DLin-D-DMA, DLin-MC3-DMA, DLin-KC2-DMA, DODMA and amino alcohol lipids. The amino alcohol cationic lipid can be the lipids described in and/or made by the methods described in US Patent Publication No. US20130150625. As a non-limiting example, the cationic lipid can be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-oc-tadeca-9,12-dien-1-yloxy]methyl}propan-1-ol (Compound 4 in US20130150625); or any pharmaceutically acceptable salt or stereoisomer thereof. Nanoparticle formulations of the present disclosure can be coated with a surfactant or polymer in order to improve the delivery of the particle. In some embodiments, the nanoparticle is coated with a hydrophilic coating such as, but not limited to, PEG coatings and/or coatings that have a neutral surface charge. The hydrophilic coatings can help to deliver nanoparticles with larger payloads such as, but not limited to, polynucleotides within the central nervous system. As a non-limiting example nanoparticles comprising a hydrophilic coating and methods of making such nanoparticles are described in US Patent Publication No. US20130183244.

The invention will be further illustrated by the following figures and examples. However, these examples and figures should not be interpreted in any way as limiting the scope of the present invention.

FIGURES

FIG. 1: Identification and effects of the p.G12R RAC2 mutation on RAC2's GTPase activity. A. Pedigrees of the three patients from two unrelated kindreds. Black boxes and black circles represent the affected male (P1) and females (P2, P3), respectively. White boxes and circles represent unaffected individuals. Arrows represent the probands, and a double horizontal bar represent consanguinity. B. A representative electropherogram of RAC2 DNA sequencing for control and patient cells, showing the c.34G>A mutation. C. A representative immunoblot of RAC2 protein expression in lysates from control fibroblasts (C1, C2) and fibroblasts derived from the affected individuals (P1, P2 and P3). The loading control corresponds to GADPH expression. D. HEK293T cells were either not transduced (NT, control) or were transduced with a lentiviral empty vector (WPI) containing the wild type (WT) form of RAC2 cDNA, the mutated form described here (G12R) or (as a positive control) the constitutively activated RAC2 GTP form (G12V). Two days after transduction, cells were recovered for analysis using the G-LISA assay (15 µg of total protein per well). The results are quoted as the mean±standard error of the mean (SEM) of three independent experiments. *p<0.001; **p<0.0001.

FIG. 2: G12R Mutation Inhibits HSPC Proliferation and Differentiation

A. Proliferation of CD34-positive cells in a 7-day culture. Flow cytometry was used to analyse the proportion (in %) of GFP+-expressing cells in the live cell (7-AAD-negative) gate. The proportions of ROS-low, DiIC1(5)-low and annexin V-positive GFP+ live cells were determined on day 4. The results are quoted as the mean±SEM of four independent experiments. B. Neutrophil differentiation in a 7-day culture. Flow cytometry was used to analyse the number of granulocytes (CD11b+CD15+) among the GFP+ live cells. The proportions of ROS low, DiIC1(5) low and annexin V+ cells among the GFP+ live cells were analysed on day 4. The results are quoted as the mean±SEM of three independent experiments. C. T cell differentiation in a 7-day culture (n=3). Flow cytometry was used to analyse the proportion of GFP+ live cells. The number of T cell progenitors (CD7+) was evaluated on day 7 in the GFP+ live cells. The results are quoted as the mean±SEM of three independent experiments. For all experiments: *p<0.05; p<0.01 and *p<0.001.

FIG. 3. Test of Molm-13 cells from acute myelogenous leukemia (AML, translocation MLL-AF9). A. Molm-13 cells were transduced in the presence of a lentiviral construct containing an empty vector (WPI) or a vector with the wild-type form of RAC2 (WT) or a vector containing the mutated form of RAC2 (G12R). The transduced cells all express a GFP reporter gene making it possible to detect by flow cytometry the % of GFP+ cells and the number of GFP+ transduced cells during a 7-day culture. B. At day 4, flow cytometry analysis was performed to evaluate the proportion of GFP+ transduced cells which enters apoptosis (% annexin V+), the mitochondrial membrane polarization (% Δ µm) and the ROS production. The results are representative of 4 independent experiments. p<0.01 and *p<0.001.

Figure 4:
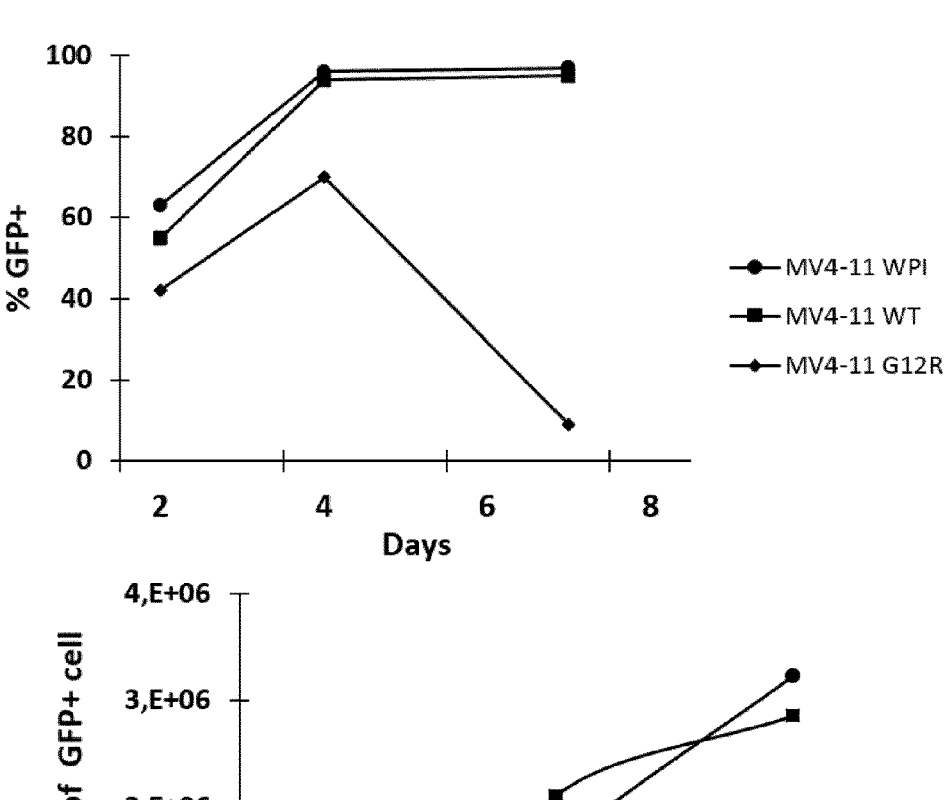

FIG. 4. Test of MV4-11 cells from AML (translocation MLL-AF4). MV4-11 cells were transduced in the presence of a lentiviral construct containing an empty vector (WPI) or a vector with the wild-type form of RAC2 (WT) or a vector containing the mutated form of RAC2 (G12R). The transduced cells all express a GFP reporter gene making it possible to detect by flow cytometry the % of GFP+ cells and the number of GFP+transduced cells during a 7 day culture. The results are representative of 2 independent experiments.

FIG. 5. Test of HL60 cells from AML. HL-60 cells were transduced in the presence of a lentiviral construct containing an empty vector (WPI) or a vector with the wild-type form of RAC2 (WT) or a vector containing the mutated form of RAC2 (G12R). Following the transduction step, cells were cultured in the presence of retinoic acid in order to induce their differentiation toward the granulocytic lineage. A-B. The transduced cells all express a GFP reporter gene making it possible to detect by flow cytometry the number of GFP+transduced cells 2 days (J2) and 4 days (J4) after the beginning of the culture and the number of granulocytes (CD11b+CD15+). The results are representative of 3 independent experiments *p<0.05 *** p<0.001. C-D. At day 4, flow cytometry analysis was performed to evaluate the proportion of cell with a low mitochondrial membrane polarisation level and a low ROS production level. The percentage of cell entering apoptosis was 2% and 10% for the WT and G12R condition, respectively. The histogramms are representative of 3 independent experiments.

FIG. 6. A. Mononuclear cells from peripheral blood from healthy donors were cultured in the presence of Phytohemagglutinin A and transduced with a lentiviral construct containing an empty vector (WPI) or a vector containing the mutated form of RAC2 (G12R). The transduced cells all express a GFP reporter gene making it possible to follow by flow cytometry the % of GFP+ cells, the number of GFP+ transduced cells and the proportion of GFP+ cells which enters apoptosis (% annexin V+). The results are representative of 2 independent experiments. B. B-EBV lines from healthy donors were transduced in the presence of a lentiviral construct containing an empty vector (WPI) or a vector containing the mutated form of RAC2 (G12R). The transduced cells all express a GFP reporter gene making it possible to follow by flow cytometry the% of GFP+ cells. The results are representative of 3 independent experiments ***p<0.001.

EXAMPLE

Material & Methods
Patients and Human Cord Blood Samples

The study was conducted in accordance with the French legislation and the principles of the Declaration of Helsinki.

Informed consent was obtained from the patients' parents or legal guardians, and the study protocol was approved by the regional independent ethics committee and the French Ministry of Research (DC 2014-2272/2015/DC-2008-329.) Primary fibroblast cell lines were obtained from skin biopsies.

Human cord blood (CB) samples eligible for research purposes were obtained from the Cord Blood Bank at St Louis Hospital (Paris, France; authorization 2014/09/23). Mononuclear cells were isolated by density separation on Lymphoprep (Abcys). CD34-positive HSPCs were sorted magnetically using the autoMACSpro separator (Miltenyi Biotec), and the cells' purity was checked with a MACSQuant analyzer (Miltenyi Biotec).

Genetic, Sequencing and Gene Expression Analysis

Genomic DNA was isolated by phenol/chloroform extraction from fibroblasts (P1, P2 and P3) or peripheral blood mononuclear cells (PBMCs) (P3 father). Whole-exome sequencing was performed with an Illumina TruSeq exome enrichment kit (Illumina), using 100 bp paired-end reads. Eighty-five percent of target regions were observed with a coverage >20×. Variant calling was not based on a particular genetic model. The G12R RAC2 variant was not found in a number of in-house and public sequence databases. Sanger sequencing confirmed the mutation in P1, P2 and P3 (ABI Prism 3700 sequencer, Life Technologies).

For Western blot analyses, primary fibroblasts from control or patients were lysed in a Tris buffer (20 mM Tris, pH 7.9; 300 mM NaCl; 1% Nonidet P-40) supplemented with protease and phosphatase inhibitors. Cell extracts were separated by SDS-PAGE, blotted, and stained with anti-RAC2 (ab154711, Abcam) or anti-GAPDH (SC-32233, Santa Cruz) antibodies. After staining with an HRP-conjugated secondary antibody, the immunoblot was developed using an ECL+ kit (Amersham). Protein levels were quantified with Fiji software.

Construction and production of the lentiviral vectors. The backbone of the replication-defective, self-inactivating pWPI lentiviral vector was provided by Addgene (https://www.addgene.org/). All the constructs (G12R, G12V, D57N and E62K) were generated by GenScript (https://www.genscript.com). Lentiviral supernatants were produced by the vector facility at SFR BioSciences Gerland-Lyon Sud (Lyon, France). All procedures with genetically modified cells were approved by the French National Biotechnology Council and the French Ministry of Research (reference: 4983/3).

RAC2 Activation Assays and Immunoblotting on the HEK293T Cell Line

The HEK293T cells were cultured overnight prior to transduction with the appropriate lentiviral supernatant at a multiplicity of infection of 20. After two days of culture, the cell pellets were frozen in liquid nitrogen. Levels of activated RAC2 were determined using the G-LISA® RAC Activation Assay Biochem Kit™ (#BK125, Cytoskeleton Inc.). The G-LISA® kit was performed according to the manufacturer's instructions, except that 10 µg/ml RAC2 specific antibody (AT2G11, sc-517424, Santa Cruz Biotechnology, Inc.) and 1/2000 HRP-conjugated anti-mouse antibody (#1721011, Bio-Rad) were used to detect the amount of captured active RAC2. The reaction was visualized by the addition of 100 µl of chromogenic substrate (1-step Ultra-TMB, 34028, Thermo Scientific) for 3 min, and stopped with 50 µl H2SO4 1N. Absorbance at 450 nm was measured using FLUOstar OPTIMA microplate reader. Whole cell extracts were obtained by lysing cells in G-LISA lysis buffer supplemented with a protease inhibitor cocktail. Proteins were separated by SDS-PAGE, and immunoblotted with anti-RAC2 (AT2G11, sc-517424, Santa Cruz Biotechnology, Inc.) or anti GAPDH (14C10, Cell Signaling Technology) antibodies. Immunoblots were revealed by chemiluminescence using the ChemiDoc MP System (Bio-Rad). Protein levels were quantified with Image Lab software.

Holotomography

To measure the refractive index within the cell (i.e. label-free visualization of cellular organelles), the cell sample was seeded into a 35-mm glass bottom-dish (Ibidi-Dishes™ #81156; Ibidi, GmbH) and placed into the viewing area of the 3D Cell Explorer microscope (Nanolive SA). Cell images were processed using STEVE software (Nanolive).

In Vitro Culture of Human Cord Blood CD34+ Cells

Cord blood CD34+ HSPCs were cultured overnight (as previously described[5]) and then transduced with the appropriated lentiviral supernatant at a multiplicity of infection of 80. After two days of culture, the GFP+ cells were measured by flow cytometry prior to in vitro culture. The CD34+ cells' ability to differentiate along the granulocyte or T cell lineage was measured as described elsewhere[6,29].

Flow Cytometry, Mitotracker DIIC1(5) and CellRox Staining

Monoclonal antibodies against CD7(MT-701), CD11b (D12), CD34 (8G12), and mouse IgG1k, IgG2a and IgG2b isotype controls, and the reagents annexin V and 7-amino-actinomycin D (7AAD) were obtained from BD Biosciences (San José, Calif.). CD15 (80H5) and mouse IgM control antibodies were purchased from Beckman Coulter (San Diego). The mitochondrial membrane potential was measured using a MitoProbe™ DiIC1(5) assay kit (M34151), and the ROS level was measured using a CellRox® assay kit (C10492), according to the manufacturer's instructions (Life Technologies). After staining, cells were analyzed on a Gallios flow cytometer, and the data were processed using Kaluza software (all from Beckman Coulter).

Homology Modelling

Three-dimensional homology models were built for the G12R mutant of human RAC2 (Uniprot P15153) using MODELLER software v20 (Webb and Sali, 2016, 2017). The crystal structure of WT human RAC2 (PDB code: 1DS6) was used as a template.

Statistical Analysis

For all analyses, three or more independent experiments were performed. Data are reported as the mean±standard error of the mean (SEM). Two-tailed, unpaired t-test was performed using Prism 4 software (GraphPad). The threshold for statistical significance was set to p<0.05.

Results

A Missense Mutation (G12R) in the RAC2 GTPase Protein Leads to a SCID Phenotype

In our cohort of patients with a SCID phenotype, a few individuals do not have yet a molecular diagnosis. Three patients from two unrelated kindreds (P1 from one kindred, and P2 and P3 as the mother and daughter from another kindred, respectively) presented with all the clinical features of RD other than deafness (FIG. 1A). As observed in patients with RD, the complete absence of neutrophils was responsible for the occurrence of severe infections earlier than is usually observed in other forms of SCID (Table 1) picard[2]. The analysis of other blood cell lineages highlighted the absence of T and B lymphocytes and circulating monocytes. Conversely, the platelet counts were normal, and haemoglobin level was slightly lower than normal in only one patient (Table 1). Overall, the peripheral cell count profile corresponded to the severe hypoplastic morphology of the patients' bone marrow (Table 1, and data not shown). Haematopoietic stem cell transplantation (HSCT) performed soon after birth was successful in P1 (previously described as P4[12]) and P2—demonstrating that the inherited defect was intrinsic and not extrinsic (i.e. not micro-environmental) (Table 1).

By performing whole-genome sequencing (WES) of the patients' fibroblasts, we identified a heterozygous missense mutation (c.34G>A, p.G12R) in the RAC2 gene as the only possible genetic cause. The mutation was confirmed by Sanger sequencing in the three patients but was absent in P3's father—the only relative from whom we could obtain a DNA sample (FIG. 1B). The presence of the same phenotype and the same RAC2 G12R missense mutation in P2 and her daughter P3 highlighted the AD inheritance pattern.

Figure 1C:
Figure 1D:
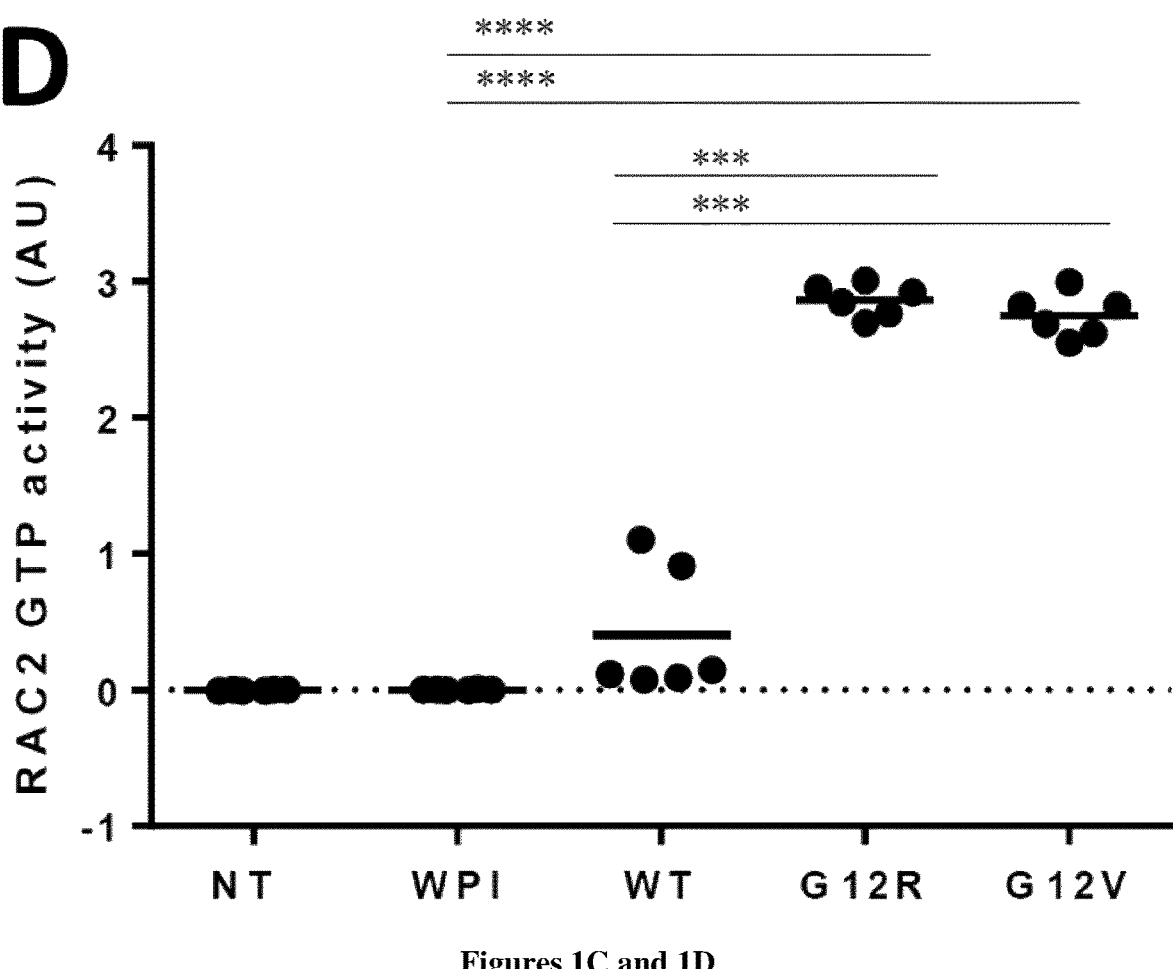

The p.G12R missense mutation is located in the G1 box—a highly conserved guanine nucleotide binding region[13]—and was not annotated in our in-house database (n=14154 in the cohort) or in the human Genome Aggregation Database (gnomAD). The mutation was predicted to be deleterious by four different in silico prediction software, including Combined Annotation Dependent Depletion. It is noteworthy that this gene mutation differed from the loss-of-function (LOF) or gain-of-function (GOF) mutations previously reported to be responsible for mild neutrophil defects and/or lymphopenia[14-18]. It is noteworthy that the G12R missense mutation was associated with normal levels of RAC2 protein expression in the patients' fibroblasts (FIG. 1C).

The G12R Mutation Located in the GDP/GTP-Binding Domain Disrupts Cell Homeostasis In order to understand the functional impact of this G12R mutation, we generated a three-dimensional homology model using wild-type (WT) RAC2's X-ray structure[19] as a template (Data not shown). A bulky, flexible arginine is predicted to block the entrance to the GDP/GTP binding pocket in the G1 box (Data not shown). Accordingly, the arginine's charged guanidinium group might disrupt the positively charged pocket and thus influence the GTP hydrolysis rate—as previously demonstrated for other small GTPases[20].

To test this model biochemically, we quantified the active RAC2 GTP-bound form in extracts of naturally RAC2-negative HEK293T cells. The cells were transduced with an empty lentiviral backbone(WPI) with green fluorescent protein (GFP) as a tracker or the vector containing either the WT form of RAC2 cDNA, the mutated form described here (G12R) or as positive control, the constitutively activated RAC2 GTP form (G12V)[21]. A high level of the active GTP-bound RAC2 form was observed with both G12V and G12R (FIG. 1D)—demonstrating that substitution by arginine at position 12 leads to sustained activation of the RAC2 signalling pathway. The G12R mutation is therefore a GOF mutation.

To determine how the expression of a constitutively active form of RAC2 impacts cell division and survival, we performed a holotomographic analysis of primary fibroblasts from P3. In agreement with the low observed cell proliferation rate in vitro (data not shown), the patient's fibroblasts were characterized by very slow cellular dynamics and fragmented nuclei that were suggestive of cytokinesis failure (Data not shown). Moreover, and in contrast to control fibroblasts, the cell shape and mitochondrial network were disrupted in P3's fibroblasts (Data not shown). These two observations highlighted a link between the G12R mutation, defective mitochondrial activity, and dramatic changes in cellular mitosis that reflect a defect in the RAC signalling pathways driving cytokinesis[22].

Figure 2A:
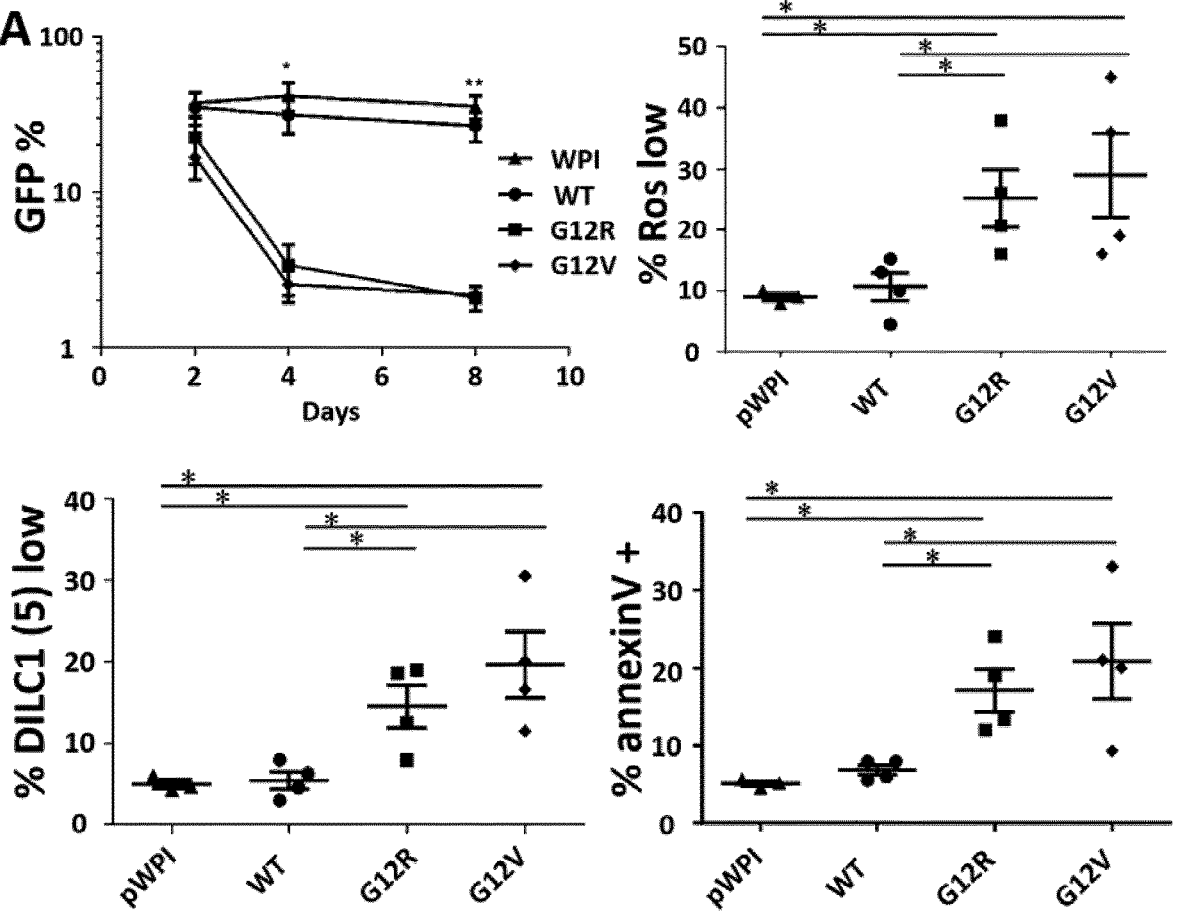
Figures 2B, 2C:
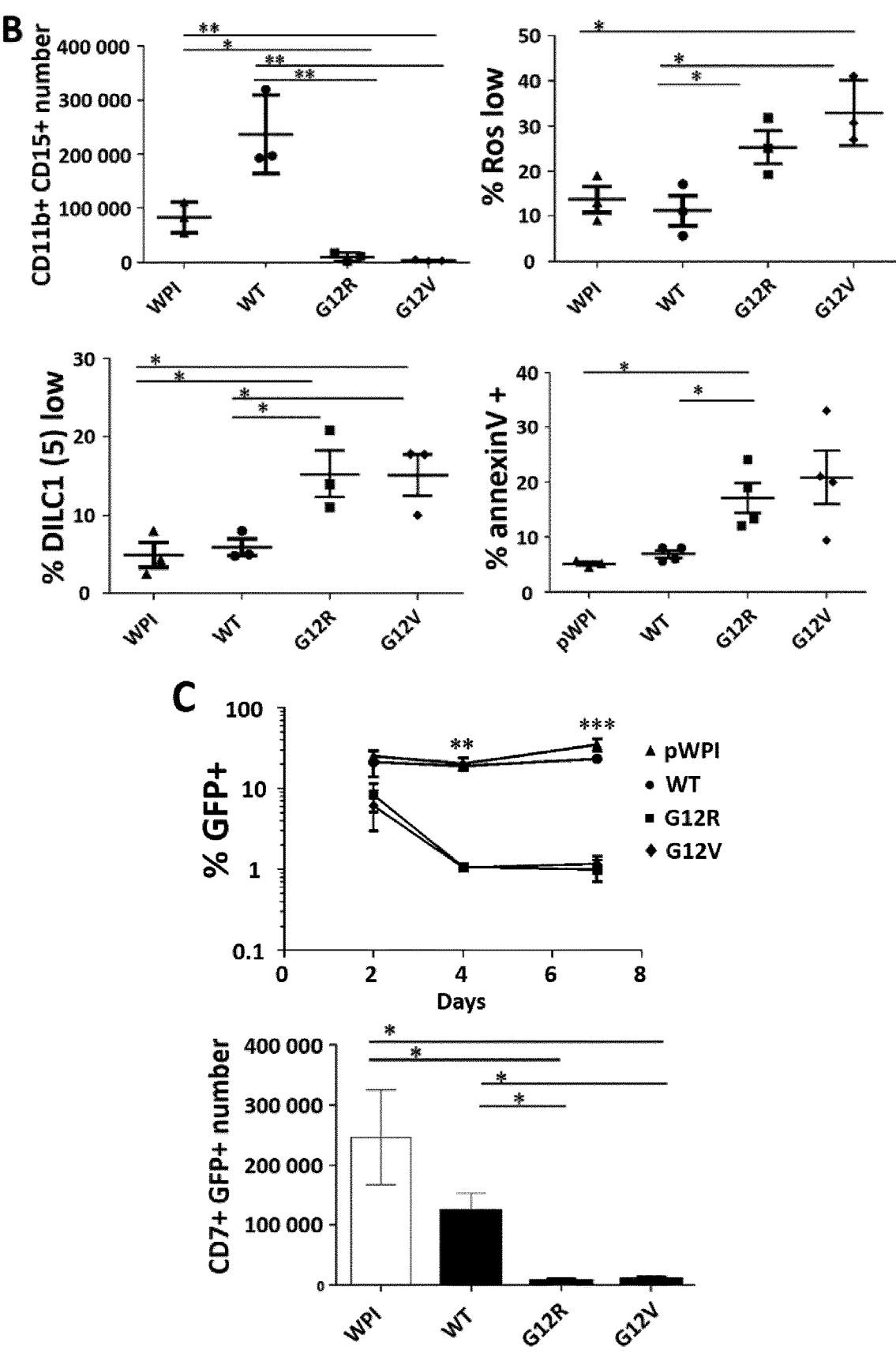

The G12R Mutation Disrupts Mitochondrial Activity and Blocks HSPC Differentiation To understand the impact of constitutive RAC2 activation on haematopoiesis, CD34-positive human cord blood HSPCs (given the absence of patient bone marrow samples) were transduced with the WPI, WT, G12R or G12V RAC2 cDNAs (with GFP as tracker) and then cultured with cytokines for 7 days (FIG. 2b). The expression of constitutively activated RAC2 forms (G12R and G12V) led to the disappearance of GFP+ transduced cells within 4 days—a time point at which reactive oxygen species (ROS) production (quantified as the proportion of "ROS low" cells) was blocked significantly, and mitochondrial membrane depolarization (the proportion of "DiIC1(5) low" cells) and apoptosis (the proportion of annexin V-positive cells) had increased significantly (FIG. 2A). It is noteworthy that these changes were not observed in the GFP-negative subset. Taken as a whole, these findings underlined the specific correlation between mutations at position 12 in the RAC2 protein and mitochondrial dysfunction. Our results are in line with previous reports indicating that (i) mitochondrial activity is required for HSPC function[23,24], and (ii) disruption of the RAC2 signalling pathway affect mitochondrial dynamics[25] and ROS production[26-28]. (FIG. 2A).

As RAC2 is highly expressed in human hematopoietic bone marrow subsets and during human thymopoiesis, we transduced HSPCs with WPI, WT, G12R or G12V RAC2 cDNAs and stimulated them to differentiate along the granulocyte, monocyte and T-lymphoid lineages, all absent in the three patients. After 7 days of culture with granulocyte-colony-stimulating factor, the GFP+CD15+CD11b+ neutrophil counts were significantly lower in the G12R and G12V conditions than in the WPI or WT conditions (FIG. 2B). The mitochondrial membrane potential and ROS production were also found to be disrupted, and were associated with elevated levels of apoptosis (FIG. 2B). Differentiation towards the monocyte lineage and differentiation in colony-forming unit assays gave similar results (data not shown). Upon exposure to the Notch ligand delta-like-4 (DL4) culture system (which enables the differentiation of HSPCs into CD7+ T-cell progenitors in 7 days[29]), the GFP+ subset count in the G12R and G12V conditions was very low (relative to the WT and WPI conditions), and GFP+CD7+ T cell progenitors were almost completely absent (FIG. 2C). These results are in line with a previous report in which expression of the G12V constitutive active form of RAC2 prevented mouse thymocytes differentiation and leads to apoptosis[30]. Taken as a whole, our results underline the key function of the GDP/GTP-bound RAC2 balance in the survival and differentiation of the lymphomyeloid compartment and emphasize the RAC2 signalling pathway's involvement in HSPC function. We next compared the impact of G12R with that of previously described LOF and GOF missense mutations in RAC2 (p.D57N and p.E62K, respectively)[14,15,18] on the proliferation of human cord blood HSPCs. During the 8-day culture, the number of GFP+-transduced HSPCs was low in the E62K and G12R groups but was significantly higher in the E62K condition than in the G12R condition. Unlike the G12R mutation, the D57N and E62K mutations had no impact on mitochondrial activity.

Taken as a whole, our observations suggest that the G12R missense mutation in RAC2 is correlated with the level of the active GTP-bound form of RAC2 and with HSPC survival and function. These findings fit with the clinical and immunological phenotype of the SCID observed in our three patients and with the less severe phenotype displayed by patients carrying E62K or D57 mutations.

The Three Types of LAM Tested (Molm13, MV4-11 and HL60)

Figure 3A:
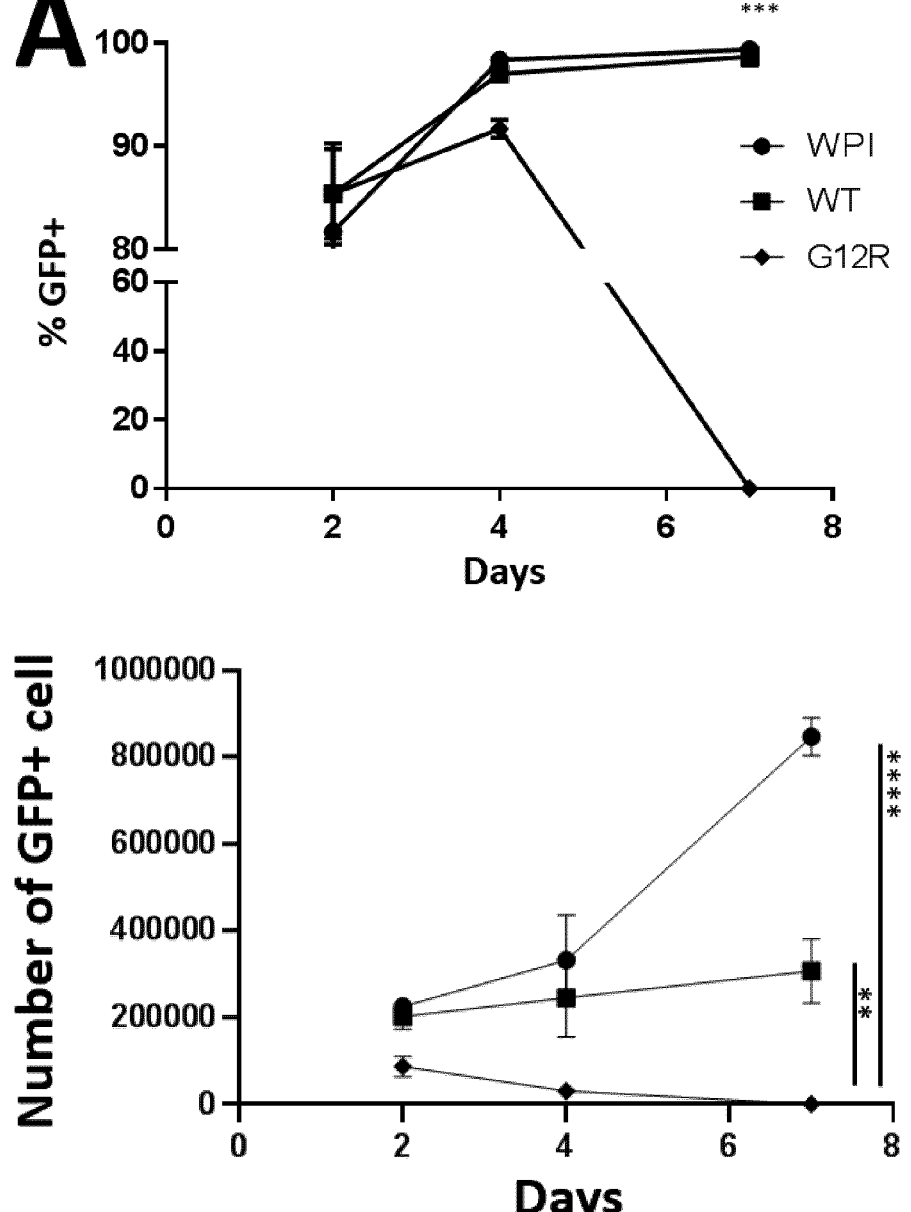
Figure 3B:
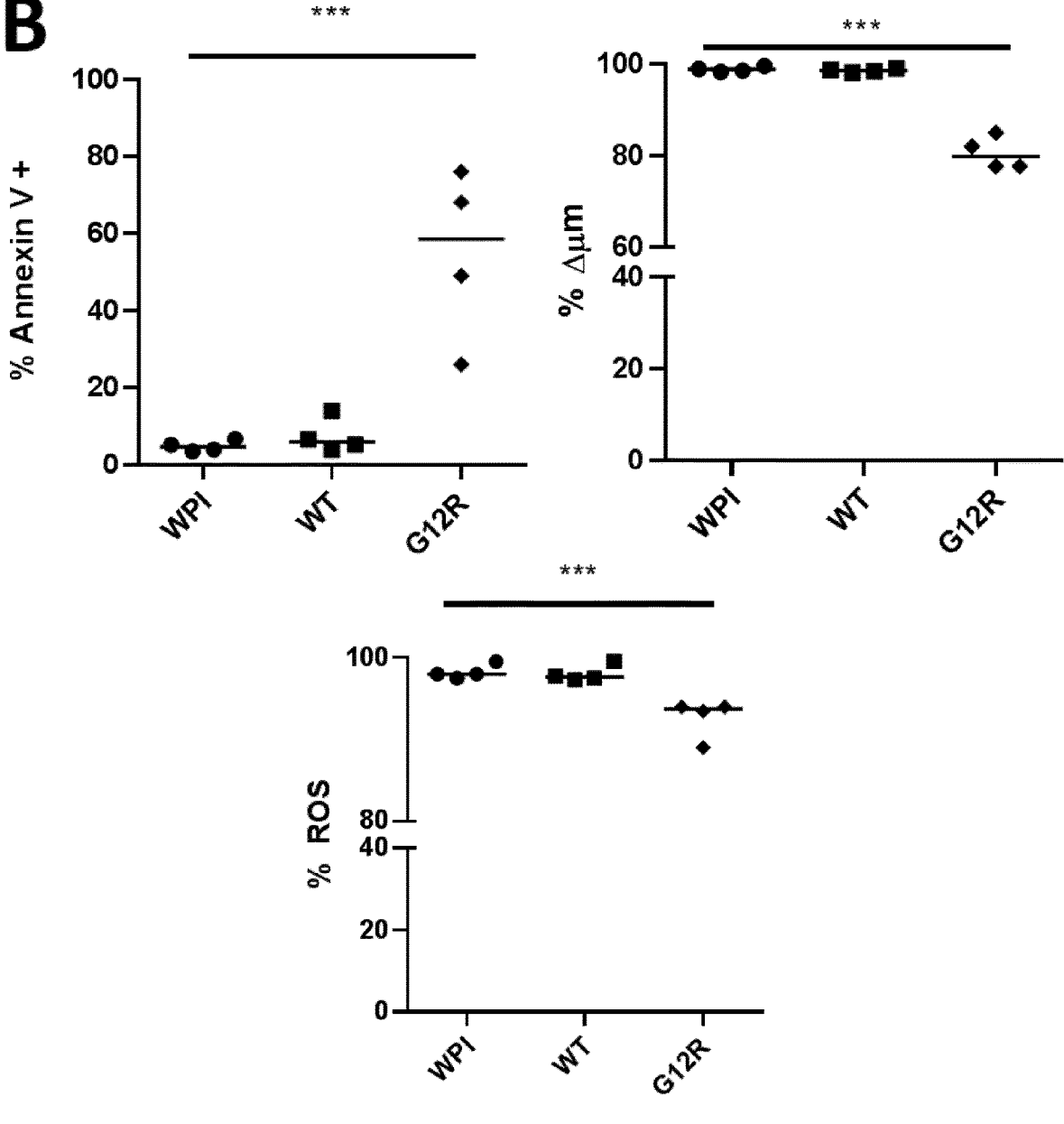

Molm-13 cells from acute myelogenous leukemia (AML, translocation MLL-AF9) were transduced in the presence of a lentiviral construct containing an empty vector (WPI), a vector containing the wild form of RAC2 (WT) or a vector containing the mutated form of RAC2 (G12R). The transduced cells all express a reporter gene GFP (green fluorescent protein) making it possible to follow by flow cytometry the percentage of GFP+ cells and the number of transduced GFP+ cells. The expression of constitutively activated RAC2 form (G12R) led to the disappearance of GFP+ transduced cells within 7 days. (FIG. 3A). This observation is correlated with an increased proportion of GFP+ apoptotic cells (% annexin V+) having defective mitochondrial membrane polarization and defective reactive oxygen species (ROS) production. (FIG. 3B).

MV4-11 cells from AML (translocation MLL-AF4) were also transduced in the presence of a lentiviral construct containing an empty vector (WPI), a vector containing the wild form of RAC2 (WT) or a vector containing the form mutated from RAC2 (G12R). The transduced cells expressing a GFP reporter gene were followed by flow cytometry and we observed a decreased percentage and number of GFP+ cells in the G12R condition (FIG. 4). The cells were also stained with May-Grunwald Giemsa and ragmentation of the nucleus was observed only in the cells transduced with the G12R construct (data not shown).

Figure 5A:
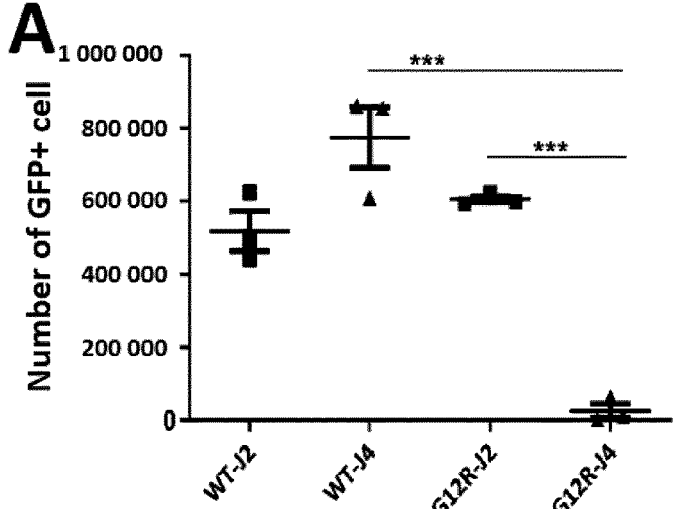

HL60 cells from AML were transduced in the presence of a lentiviral construct containing the wild form of RAC2 (WT) or a vector containing the mutated form of RAC2 (G12R). After transduction, the cells were cultured for 4 days in the presence of retinoic acid to induce their differentiation into granulocytes (CD11b+CD15+). The number of GFP+ cells was measured at day 2 (J2) and day 4 (J4) and the number of granulocytes at day 4. As observed on FIGS. 5A and 5B, the number of GFP+ and CD11b+CD15+ cells was drastically reduced in the G12R condition as compared to the WT condition. This observation was correlated with a higher mitochondrial membrane depolarisation (quantified as the proportion of DILC low cells; FIG. 5C) and a higher proportion of cells unable to produce ROS (quantified as the % of ROS low; FIG. 5D). Of note, the proportion of GFP+ cells entering apoptosis was 2% and 10% for the WT and G12R condition, respectively. The cells were also stained with May-Grünwald Giemsa and fragmented nuclei were only observed in the cells transduced with the G12R construct.

Figure 6A:
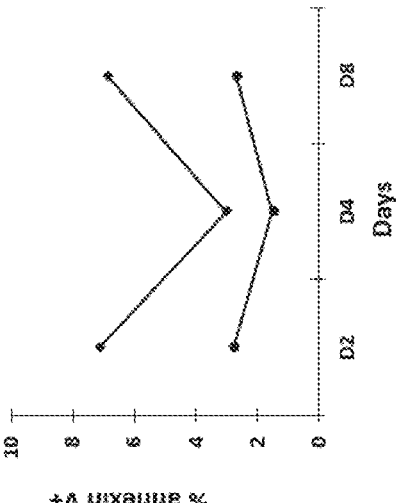
Figure 6A:
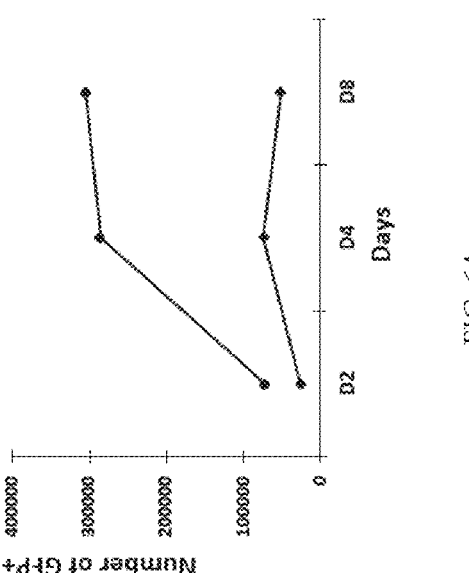
Figure 6B:
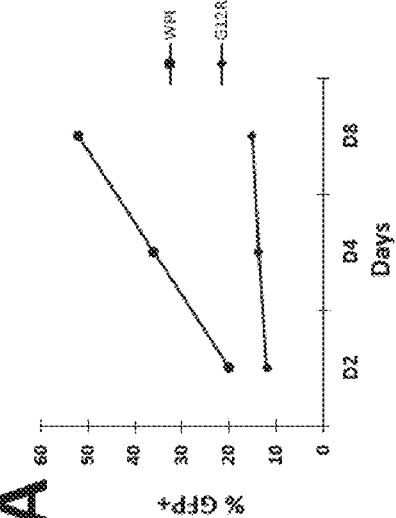
Figure 6B:
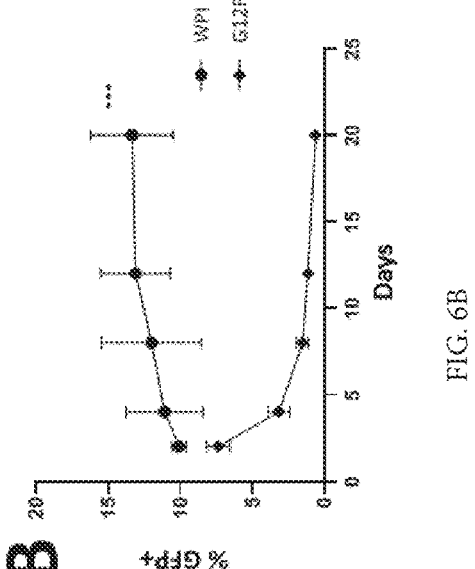

We also studied the effect of the RAC2 G12R missense mutation on primary cells. Briefly, mononuclear cells from healthy donors were transduced in the presence of a lentiviral construct containing an empty vector (WPI) or a vector containing the mutated form of RAC2 (G12R). The GFP+ transduced were followed by flow cytometry during a 8-day culture. As observed on FIG. 6A, the % and number of GFP+ cells were drastically reduced in the G12R condition as compared with the control condition. This observation is associated with a higher % of apoptotic cells (FIG. 6A). B-EBV lines from healthy donors were also transduced in the presence of a lentiviral construct containing an empty vector (WPI) or a vector containing the mutated form of RAC2 (G12R). In the time-course kinetic represented on FIG. 6B, the % of GFP+ cells is significantly decreased in the G12R condition Discussion:

In three patients with SCID, we identified a heterozygous, dominant missense mutation (p.G12R) in the highly conserved G1 box domain of the RAC2 protein. The mutation affected the innate and adaptive immune systems. Given the severity of the clinical presentation, the patients had to undergo HSCT in the first few weeks of life. The observation of AD inheritance broadens the clinical spectrum of RD. We now distinguish between two forms of RD: a recessive syndromic form associated with deafness and AK2 mutations (type I), and a non-syndromic form (without deafness) specifically associated with the AD G12R mutation in RAC2 (type II). The absence of sensorineural hearing loss in the type II AD-SCID form might be due to the specific expression of RAC2 in the hematopoietic lineage and the fact that RAC1 and RAC3 (but not RAC2) are the RAC GTPases involved in the development of the mouse inner ear[31].

The G12R-RAC2 mutation identified here had a drastic effect on cell proliferation and survival—especially in HSPCs. Furthermore, the mutation disrupted mitochondrial activity in HSPCs and impaired cell differentiation toward lymphoid and myeloid lineages. These features might explain the absence of circulating lymphocytes and neutrophils in our three patients, and highlight the non-redundant regulatory role of RAC2 at different haematopoietic checkpoints.

Surprisingly, in our experiments, the D57N LOF variant has no impact on the HSPC pool, and the E62K GOF variant only has a moderate effect (relative to G12R). Taken as a whole, our findings emphasize that the various RAC2 mutations differ in their effects on HSPCs, which probably accounts for the broad spectrum of clinical phenotypes observed in patients with RAC2 defects (ranging from neutrophil defects and/or leukopenia—without any reported alteration of haematopoiesis—to the SCID form with bone-marrow hypoplasia we described here). This type of heterogeneity has already been reported for RAG1 mutations, where the phenotype ranges from autoimmune disease to SCID[32].

The location of the amino-acid substitution (inside the GDP/GTP binding pocket (G12R) or in the switch II domain (E62K)) might explain the difference between these two GOF mutations. This hypothesis is in line with (i) the high level of the active (GTP-bound) form of RAC2 observed in the G12R condition, relative to its absence in the E62K condition, and (ii) the low level of RAC2 protein expression observed in the E62K condition—suggesting that glutamate substitution at position 62 may influence the protein's stability. Consequently, we suggest that G12R mutation is the only one able to activate downstream targets in a constitutive, sustained manner. Our results for the E62K variant differ those described by Hsu et al[18] as they evaluated the GTP binding capacity of purified E62K protein; here, we measured RAC2 GTP activity in a cell lysate. In light of these results, the two GOF mutations do not drive the same level of RAC2 GTP activity and the G-LISA assay appears to be an appropriate method for measuring the level of RAC2 activation in live cells.

In summary, the p.G12R RAC2 mutation has a drastic impact on the maintenance and differentiation of the HSPC compartment, and might thus explain the severity of the patients' clinical and immunological phenotype. To the best of our knowledge, the present study is the first to report an AD form of SCID and physicians should consider RAC2 gene sequencing for patients with SCID and RD clinical presentation. We also observed a drastic impact of the G12R missense mutation in various cell lines (B-EBV, AML) or mature primary cells suggesting that targeting the GDP/GTP binding domain of RAC2 protein could represent a novel therapeutic strategy to induce leukemic cells death.

4. Pannicke, U. et al. Reticular dysgenesis (aleukocytosis) is caused by mutations in the gene encoding mitochondrial adenylate kinase 2. Nat. Genet. 41, 101-5 (2009).

TABLE 1

Haematological characteristics and outcomes for the three patients

| Patients (age at presentation) | P1 (3 days) | P2 (10 days) | P3 (9 days) | Age matched control value |
|---|---|---|---|---|
| Infection at birth | Sepsis | coloured amniotic fluid sepsis/pneumonia | Sepsis/ meningitis brain abscesses | |
| White blood cells (×10$^{-9}$/l) | 0.6 | 0.3 | 0.5 | 7-18 |
| Lymphocytes (×10$^{-9}$/l) | 0.4 | 0.1 | 0.5 | 3.4-7.6 |
| B lymphocytes (×10$^{-9}$/l) | 0.09 | 0.004 | 0 | 0.3-2 |
| T lymphocytes (×10$^{-9}$/l) | 0.24 | 0.07 | 0 | 2.5-5.5 |
| Monocytes (×10$^{-9}$/l) | 0.01 | NE | 0 | 0.1-1.1 |
| Neutrophils (×10$^{-9}$/l) | 0.2 | NE | 0 | 1.5-8.5 |
| Platelets (×10$^{-9}$/l) | 248 | 220 | 429 | 175-500 |
| Haemoglobin (g/dl) | 18 | 13 | 10 | 12.5-16.6 |
| Bone marrow aspirate | Hypoplasia | Hypoplasia | Hypoplasia | |
| HSCT (age at transplantation, months) Conditioning regimen | 1$^{st}$ T-depleted HSCT (3 M) Busulfan 8 mg/kg Endoxan 200 mg/kg SAL 25 mg/kg 2$^{nd}$ T-depleted HSCT (6 M) Busulfan 16 mg/kg Cyclophosphamide 200 mg/kg SAL 25 mg/kg | HSCT (2 M) Busulfan 8 mg/kg Endoxan 50 mg/kg | 1$^{st}$ T-depleted HSCT (2 M) Busulfan 3.6 mg/kg Fludarabine 160 mg/m$^2$ SAL 5 mg/kg 2$^{nd}$ HSCT (3 M) Fludarabine 120 mg/m$^2$ SAL 5 mg/kg | |
| Donor cells | 1$^{st}$ HSCT: MMFD/f 2$^{nd}$ HSCT: MMFD/f | MMFD/f | 1$^{st}$ HSCT: MMFD/f 2$^{nd}$ HSCT: MMFD/f | |
| Outcome | A/W | GVHD resolved at D120; A/W | Graft failure; death (5.5 M post-HSCT) | |

BM = bone-marrow;
HSCT = haematopoietic stem cell transplantation;
M = months;
ALS: anti-lymphocyte serum;
MMFD/f: mismatched family donor/father;
GVHD: graft versus host disease;
A/W: alive and we

REFERENCES

Throughout this application, various references describe the state of the art to which this invention pertains. The disclosures of these references are hereby incorporated by reference into the present disclosure.

1. Fischer, A., Notarangelo, L. D., Neven, B., Cavazzana, M. & Puck, J. M. Severe combined immunodeficiencies and related disorders. Nat. Rev. Dis. Prim. 1, 15061 (2015).
2. Picard, C. et al. International Union of Immunological Societies: 2017 Primary Immunodeficiency Diseases Committee Report on Inborn Errors of Immunity. J. Clin. Immunol. 38, 96-128 (2018).
3. de VAAL, O. & SEYNHAEVE, V. Reticular dysgenesia. Lancet (London, England) 2, 1123-5 (1959).
5. Lagresle-Peyrou, C. et al. Human adenylate kinase 2 deficiency causes a profound hematopoietic defect associated with sensorineural deafness. Nat. Genet. 41, 106[-11] (2009).
6. Six, E. et al. AK2 deficiency compromises the mitochondrial energy metabolism required for differentiation of human neutrophil and lymphoid lineages. Cell Death Dis. 6, e1856 (2015).
7. Troeger, A. & Williams, D. A. Hematopoietic-specific Rho GTPases Rac2 and RhoH and human blood disorders. Exp. Cell Res. 319, 2375-83 (2013).
8. Nayak, R. C., Chang, K.-H., Vaitinadin, N.-S. & Cancelas, J. A. Rho GTPases control specific cytoskeleton-dependent functions of hematopoietic stem cells. Immunol. Rev. 256, 255-68 (2013).

9. Gu, Y. et al. Hematopoietic cell regulation by Rac1 and Rac2 guanosine triphosphatases. Science 302, 445-9 (2003).

10. Shirsat, N. V, Pignolo, R. J., Kreider, B. L. & Rovera, G. A member of the ras gene superfamily is expressed specifically in T, B and myeloid hemopoietic cells. Oncogene 5, 769-72 (1990).

11. Gu, Y. et al. Rac2, a hematopoiesis-specific Rho GTPase, specifically regulates mast cell protease gene expression in bone marrow-derived mast cells. Mol. Cell. Biol. 22, 7645-57 (2002).

12. André-Schmutz, I. et al. Immune reconstitution without graft-versus-host disease after haemopoietic stem-cell transplantation: a phase 1/2 study. Lancet 360, 130-7 (2002).

13. Olson, M. F. Rho GTPases, their post-translational modifications, disease-associated mutations and pharmacological inhibitors. Small GTPases 9, 203-215 (2018).

14. Ambruso, D. R. et al. Human neutrophil immunodeficiency syndrome is associated with an inhibitory Rac2 mutation. Proc. Natl. Acad. Sci. U.S.A. 97, 4654-9 (2000).

15. Accetta, D. et al. Human phagocyte defect caused by a Rac2 mutation detected by means of neonatal screening for T-cell lymphopenia. J. Allergy Clin. Immunol. 127, 535-538. e1-2 (2011).

16. Alkhairy, 0. K. et al. RAC2 loss-of-function mutation in 2 siblings with characteristics of common variable immunodeficiency. J. Allergy Clin. Immunol. 135, 1380-4. e1-5 (2015).

17. Lougaris, V. et al. A monoallelic activating mutation in RAC2 resulting in a combined immunodeficiency. J. Allergy Clin. Immunol. (2019). doi:10.1016/j.jaci.2019.01.001

18. Hsu, A. P. et al. Dominant activating RAC2 mutation with lymphopenia, immunodeficiency and cytoskeletal defects. Blood (2019). doi:10.1182/blood-2018-11-886028

19. Scheffzek, K., Stephan, I., Jensen, 0. N., Illenberger, D. & Gierschik, P. The Rac-RhoGDI complex and the structural basis for the regulation of Rho proteins by RhoGDI. Nat. Struct. Biol. 7, 122-6 (2000).

20. Hunter, J. C. et al. Biochemical and Structural Analysis of Common Cancer-Associated KRAS Mutations. Mol. Cancer Res. 13, 1325-1335 (2015).

21. Illenberger, D. et al. Rac2 regulation of phospholipase C-beta 2 activity and mode of membrane interactions in intact cells. J. Biol. Chem. 278, 8645-52 (2003).

22. Canman, J. C. et al. Inhibition of Rac by the GAP activity of centralspindlin is essential for cytokinesis. Science 322, 1543-6 (2008).

23. Bigarella, C. L., Liang, R. & Ghaffari, S. Stem cells and the impact of ROS signaling. Development 141, 4206-18 (2014).

24. Ansô, E. et al. The mitochondrial respiratory chain is essential for haematopoietic stem cell function. Nat. Cell Biol. 19, 614-625 (2017).

25. Capala, M. E. et al. Mitochondrial Dysfunction in Human Leukemic Stem/Progenitor Cells upon Loss of RAC2. PLoS One 10, e0128585 (2015).

26. Pei, H. et al. RAC2-P38 MAPK-dependent NADPH oxidase activity is associated with the resistance of quiescent cells to ionizing radiation. Cell Cycle 16, 113-122 (2017).

27. Tao, W. et al. The TRQQKRP motif located near the C-terminus of Rac2 is essential for Rac2 biologic functions and intracellular localization. Blood 100, 1679-88 (2002).

28. Nieborowska-Skorska, M. et al. Rac2-MRC-cIII-generated ROS cause genomic instability in chronic myeloid leukemia stem cells and primitive progenitors. Blood 119, 4253-63 (2012).

29. Reimann, C. et al. Human T-Lymphoid Progenitors Generated in a Feeder-Cell-Free Delta-Like-4 Culture System Promote T-Cell Reconstitution in NOD/SCID/γc-/- Mice. Stem Cells 30, 1771-1780 (2012).

30. Lorès, P., Morin, L., Luna, R. & Gacon, G. Enhanced apoptosis in the thymus of transgenic mice expressing constitutively activated forms of human Rac2GTPase. Oncogene 15, 601-605 (1997).

31. Grimsley-Myers, C. M., Sipe, C. W., Wu, D. K. & Lu, X. Redundant functions of Rac GTPases in inner ear morphogenesis. Dev. Biol. 362, 172-186 (2012).

32. Notarangelo, L. D., Kim, M.-S., Walter, J. E. & Lee, Y. N. Human RAG mutations: biochemistry and clinical implications. Nat. Rev. Immunol. 16, 234-246 (2016).

The invention claimed is:

1. A method of treating acute myelogenous leukemia (AML) in a patient that has AML comprising administering to the patient a therapeutically effective amount of i) a polypeptide comprising the amino acid sequence as set forth in SEQ ID NO:1 wherein the amino residue (G) at position 12 is mutated to R, or ii) a polynucleotide encoding for a polypeptide comprising the amino acid sequence as set forth in SEQ ID NO:1 wherein the amino residue (G) at position 12 is mutated to R.

2. The method according to claim 1 wherein the polynucleotide is a messenger RNA (mRNA).

3. The method according to claim 1 wherein the polynucleotide is inserted in a vector.

4. The method according to claim 1 wherein the polypeptide or the polynucleotide is conjugated to at least one other molecule selected from the group consisting of polynucleotides, polypeptides, lipids, lectins, carbohydrates, vitamins, cofactors, and drugs.

5. The method according to claim 1 wherein the polypeptide or polynucleotide is formulated with lipidoids.

6. The method according to claim 1, wherein the polypeptide or the polynucleotide is formulated using one or more liposomes, lipoplexes, or lipid nanoparticles.

*    *    *    *    *